US007271363B2

(12) United States Patent
Lee et al.

(10) Patent No.: US 7,271,363 B2
(45) Date of Patent: Sep. 18, 2007

(54) PORTABLE MICROWAVE PLASMA SYSTEMS INCLUDING A SUPPLY LINE FOR GAS AND MICROWAVES

(75) Inventors: Sang Hun Lee, Austin, TX (US); Jay Joongsoo Kim, San Jose, CA (US); Togo Kinoshita, Wakayama (JP)

(73) Assignees: Noritsu Koki Co., Ltd., Wakayama-shi (JP); Amarante Technologies, Inc., Santa Clara, CA (US)

( * ) Notice: Subject to any disclaimer, the term of this patent is extended or adjusted under 35 U.S.C. 154(b) by 66 days.

(21) Appl. No.: 10/931,223

(22) Filed: Sep. 1, 2004

(65) Prior Publication Data

US 2006/0081565 A1 Apr. 20, 2006

(51) Int. Cl.
*B23K 10/00* (2006.01)
*A61B 18/18* (2006.01)

(52) U.S. Cl. .......................... 219/121.43; 219/121.51; 219/121.36; 219/121.52; 219/121.48; 219/121.75; 315/111.51; 606/37; 606/40

(58) Field of Classification Search ........... 219/121.51, 219/121.55, 121.52, 121.48, 121.75, 121.43; 118/723 MW
See application file for complete search history.

(56) References Cited

U.S. PATENT DOCUMENTS 3,353,060 A 11/1967 Yamamoto et al.
3,903,891 A * 9/1975 Brayshaw .................... 606/27
4,207,286 A 6/1980 Gut Boucher
4,473,736 A * 9/1984 Bloyet et al. .......... 219/121.48
4,611,108 A * 9/1986 Leprince et al. ....... 219/121.48
4,781,175 A * 11/1988 McGreevy et al. ........... 606/40
4,976,920 A 12/1990 Jacob (Continued)

FOREIGN PATENT DOCUMENTS

DE 44 08 301 A 9/1994

(Continued)

OTHER PUBLICATIONS

K. Kelly-W et al., "Room Temperature Sterilization of Surfaces and Fabrics With a One Atmosphere Uniform Glow Discharge Plasma", Journal of Industrial Microbiology & Biotechnology, 1998, pp. 69-74, vol. 20, Society for Industrial & Microbiology.

(Continued)

*Primary Examiner*—Stephen J. Ralis
(74) *Attorney, Agent, or Firm*—Smith Patent Office

(57) ABSTRACT

Portable microwave plasma systems including supply lines for providing microwaves and gas flow are disclosed. The supply line includes at least one gas line or conduit and a microwave coaxial cable. A portable microwave plasma system includes a microwave source, a waveguide-to-coax adapter and a waveguide that interconnects the microwave source with the waveguide-to-coax adapter, a portable discharge unit and the supply line. The portable discharge unit includes a gas flow tube coupled to the supply line to receive gas flow and a rod-shaped conductor that is axially disposed in the gas flow tube and has an end configured to receive microwaves from the microwave coaxial cable and a tapered tip positioned adjacent the outlet portion of the gas flow tube. The tapered tip is configured to focus microwave traveling through the rod-shaped conductor and generate plasma from the gas flow.

49 Claims, 6 Drawing Sheets

U.S. PATENT DOCUMENTS

| | | | |
|---|---|---|---|
| 5,084,239 A | | 1/1992 | Moulton et al. |
| 5,170,098 A | | 12/1992 | Dutton et al. |
| RE34,780 E | * | 11/1994 | Trenconsky et al. .......... 606/49 |
| 5,503,676 A | | 4/1996 | Shufflebotham et al. |
| 5,565,118 A | * | 10/1996 | Asquith et al. ........ 219/121.57 |
| 5,573,682 A | | 11/1996 | Beason, Jr. et al. |
| 5,734,143 A | * | 3/1998 | Kawase et al. ........ 219/121.43 |
| 5,741,460 A | | 4/1998 | Jacob et al. |
| 5,750,072 A | | 5/1998 | Sangster et al. |
| 5,793,013 A | * | 8/1998 | Read et al. ............ 219/121.48 |
| 5,825,485 A | | 10/1998 | Cohn et al. |
| 5,869,401 A | | 2/1999 | Brunemeier et al. |
| 5,928,527 A | | 7/1999 | Li et al. |
| 5,938,854 A | | 8/1999 | Roth |
| 5,961,921 A | | 10/1999 | Addy et al. |
| 5,977,715 A | | 11/1999 | Li et al. |
| 5,980,768 A | | 11/1999 | Abraham |
| 6,016,766 A | | 1/2000 | Pirkle et al. |
| 6,017,825 A | | 1/2000 | Kim et al. |
| 6,030,579 A | | 2/2000 | Addy et al. |
| 6,068,817 A | | 5/2000 | Addy et al. |
| 6,080,270 A | | 6/2000 | Tabrez et al. |
| 6,165,910 A | | 12/2000 | Flanner et al. |
| 6,170,668 B1 | | 1/2001 | Babko-Malyi |
| 6,200,651 B1 | | 3/2001 | Roche et al. |
| 6,209,551 B1 | | 4/2001 | Yang et al. |
| 6,221,268 B1 | | 4/2001 | Li et al. |
| 6,221,792 B1 | | 4/2001 | Yang et al. |
| 6,225,593 B1 | | 5/2001 | Howieson et al. |
| 6,228,330 B1 | | 5/2001 | Herrmann et al. |
| 6,235,640 B1 | | 5/2001 | Ebel et al. |
| 6,309,979 B1 | | 10/2001 | Patrick et al. |
| 6,337,277 B1 | | 1/2002 | Chou et al. |
| 6,363,882 B1 | | 4/2002 | Hao et al. |
| 6,388,225 B1 | * | 5/2002 | Blum et al. ............ 219/121.48 |
| 6,410,451 B2 | | 6/2002 | Nguyen et al. |
| 6,441,554 B1 | | 8/2002 | Nam et al. |
| 6,573,731 B1 | | 6/2003 | Verdeyen et al. |
| 6,677,550 B2 | | 1/2004 | Fornsel et al. |
| 6,727,148 B1 | | 4/2004 | Setton |
| 6,792,742 B2 | | 9/2004 | Ekkert |
| 6,812,895 B2 | * | 11/2004 | Anderson et al. ........... 343/701 |
| 6,958,063 B1 | * | 10/2005 | Soll et al. ..................... 606/41 |
| 7,189,939 B2 | * | 3/2007 | Lee et al. .............. 219/121.36 |
| 2002/0027135 A1 | * | 3/2002 | Fagrell et al. .............. 219/690 |
| 2003/0052612 A1 | * | 3/2003 | Tanabe ........................ 315/39 |
| 2003/0155332 A1 | * | 8/2003 | Datta et al. ............ 219/121.52 |
| 2004/0030334 A1 | * | 2/2004 | Quick et al. .................. 606/45 |
| 2004/0172580 A1 | * | 9/2004 | Kabune et al. ............. 714/699 |
| 2004/0173580 A1 | * | 9/2004 | Carr ........................ 219/121.4 |
| 2006/0021581 A1 | * | 2/2006 | Lee et al. ........... 118/723 MW |

FOREIGN PATENT DOCUMENTS

| | | | |
|---|---|---|---|
| DE | 101 64 120 | A | 7/2003 |
| JP | 43-24312 | B | 10/1968 |
| JP | 63-50478 | A | 3/1988 |
| JP | 03-70375 | A | 3/1991 |
| JP | 03-241739 | A | 10/1991 |
| JP | 05-82449 | A | 4/1993 |
| JP | 05-275191 | A | 10/1993 |
| JP | 06-5384 | A | 1/1994 |
| JP | 06-263120 | A | 9/1994 |
| JP | 07-40056 | A | 2/1995 |
| JP | 07-153593 | A | 6/1995 |
| JP | 08-508362 | A | 9/1996 |
| JP | 08-319553 | A | 12/1996 |
| JP | 11-8093 | A | 1/1999 |
| JP | 11-21496 | A | 1/1999 |
| JP | 11-224795 | A | 8/1999 |
| JP | 2000-150484 | A | 5/2000 |
| JP | 2000-353689 | A | 12/2000 |
| JP | 2001-54556 | A | 2/2001 |
| JP | 2001-512341 | A | 8/2001 |
| JP | 2001-281284 | A | 10/2001 |
| JP | 2003-135571 | A | 5/2003 |
| JP | 2003-518317 | A | 6/2003 |
| JP | 2003-210556 | A | 7/2003 |
| JP | 2004-45262 | A | 12/2004 |
| WO | WO98/35618 | A | 8/1998 |
| WO | WO99/04606 | A | 1/1999 |
| WO | WO 01/06268 | A | 1/2001 |
| WO | WO 01/06402 | A | 1/2001 |
| WO | WO 01/43512 | A | 6/2001 |

OTHER PUBLICATIONS

T. Wu et al., "A Large-Area Plasma Source Excited by a Tunable Surface Wave Cavity", Review of Scientific Instruments, May 1999, pp. 2331-2337, vol. 70, No. 5, American Institute of Physics.

K. Kelly-W et al., "Use of a One Atmosphere Uniform Glow Discharge Plasma to Kill a Broad Spectrum of Microorganisms", Journal of Vacuum Science Technology, Jul./Aug. 1999, pp. 1539-1544, vol. 17 No. 4, American Vacuum Society.

J. Sorosnenko et al., "Sterilization of Medical Products in Low-Pressure Glow Discharges", Plasma Physics Reports, 2000, pp. 792-800, vol. 26, No. 9, Maik "Nauka/Interperiodica".

J. Gerling, "Waveguide Components and Configurations for Optimal Performance in Microwave Hearing Systems", 2000, pp. 1-8, Gerling Applied Engineering, Inc.

P. Woskov et al., "Large Electrodless Plasmas at Atmospheric Pressure Sustained by a Microwave Waveguide", Palsma Science and Fusion Center, Massachusetts Institute of Technology, Jan. 2002, pp. 1-8, to be published in IEEE Transactions on Plasma Science.

S. Moon et al., "Characteristics of an Atmospheric Microwave-Induced Plasma Generated in Ambient Air by an Argon Discharge Excited in an Open-Ended Dielectric Discharge Tube", Physics of Plasmas, Sep. 2002, pp. 4045-4051, vol. 9, No. 9, American Institute of Physics.

J. Gerling, "Equipment and Methods for Waveguide Power Measurements in Microwave Heating Applications", 2002, pp. 1-8, Gerling Applied Engineering, Inc.

C. Kuruger et al., "Nonequilibrium Discharges in Air and Nitrogen Plasmas at Atmospheric Pressure", Pure Applied Chemistry, 2002, pp. 337-347, vol. 74, No. 3, IUPAC.

D. Korzec et al., "Free-Standing Microwave Excited Plasma Beam", Plasma Sources Science and Technology, Aug. 2003, pp. 523-532, vol. 12, Institute of Physics Publishing.

B. Park et al., "Sterilization Using a Microwave-Induced Argon Plasma System at Atmospheric Pressure", Physics of Plasmas, Nov. 2003, pp. 4539-4544, vol. 10, No. 11, American Institute of Physics.

V. Khomich et al., "Investigation of Principal Factors of the Sterilization by Plasma DC Glow Discharge", Institute of Physics NAS Ukraine, Ukraine, date unknown.

* cited by examiner

PORTABLE MICROWAVE PLASMA SYSTEMS INCLUDING A SUPPLY LINE FOR GAS AND MICROWAVES

BACKGROUND OF THE INVENTION

1. Field of the Invention

The present invention relates to plasma generating systems, and more particularly to a portable microwave plasma discharge unit.

2. Discussion of the Related Art

In recent years, the progress on producing plasma has been increasing. Typically, plasma consists of positive charged ions, neutral species and electrons. In general, plasmas may be subdivided into two categories: thermal equilibrium and thermal non-equilibrium plasmas. Thermal equilibrium implies that the temperature of all species including positive charged ions, neutral species, and electrons, is the same.

Plasmas may also be classified into local thermal equilibrium (LTE) and non-LTE plasmas, where this subdivision is typically related to the pressure of the plasmas. The term "local thermal equilibrium (LTE)" refers to a thermodynamic state where the temperatures of all of the plasma species are the same in the localized areas in the plasma.

A high plasma pressure induces a large number of collisions per unit time interval in the plasma, leading to sufficient energy exchange between the species comprising the plasma, and this leads to an equal temperature for the plasma species. A low plasma pressure, on the other hand, may yield one or more temperatures for the plasma species due to insufficient collisions between the species of the plasma.

In non-LTE, or simply non-thermal plasmas, the temperature of the ions and the neutral species is usually less than 100° C., while the temperature of the electrons can be up to several tens of thousand degrees in Celsius. Therefore, non-LTE plasma may serve as highly reactive tools for powerful and also gentle applications without consuming a large amount of energy. This "hot coolness" allows a variety of processing possibilities and economic opportunities for various applications. Powerful applications include metal deposition systems and plasma cutters, and gentle applications include plasma surface cleaning systems and plasma displays.

One of these applications is plasma sterilization, which uses plasma to destroy microbial life, including highly resistant bacterial endospores. Sterilization is a critical step in ensuring the safety of medical and dental devices, materials, and fabrics for final use. Existing sterilization methods used in hospitals and industries include autoclaving, ethylene oxide gas (EtO), dry heat, and irradiation by gamma rays or electron beams. These technologies have a number of problems that must be dealt with and overcome and these include issues such as thermal sensitivity and destruction by heat, the formation of toxic byproducts, the high cost of operation, and the inefficiencies in the overall cycle duration. Consequently, healthcare agencies and industries have long needed a sterilizing technique that could function near room temperature and with much shorter times without inducing structural damage to a wide range of medical materials including various heat sensitive electronic components and equipment. Thus, there is a need for devices that can generate atmospheric pressure plasma as an effective and low-cost sterilization source, and more particularly, there is a need for portable atmospheric plasma generating devices that can be quickly applied to sterilize infected areas, such as wounds on human body in medical, military or emergency operations.

Several portable plasma systems have been developed by the industries and by national laboratories. An atmospheric plasma system, as described in a technical paper by Schütze et al., entitled "Atmospheric Pressure Plasma Jet: A review and Comparison to Other Plasma Sources," IEEE Transactions on Plasma Science, Vol. 26, No. 6, December 1998, are 13.56 MHz RF based portable plasma systems. ATMOFLO™ Atmospheric Plasma Products, manufactured by Surfx Technologies, Culver City, Calif., are also portable plasma systems based on RF technology. The drawbacks of these conventional Radio Frequency (RF) systems are the component costs and their power efficiency due to an inductive coupling of the RF power. In these systems, low power efficiency requires higher energy to generate plasma and, as a consequence, this requires a cooling system to dissipate wasted energy. Due to this limitation, the RF portable plasma system is somewhat bulky and not suitable for a point-of-use system. Thus, there is the need for portable plasma systems based on a heating mechanism that is more energy efficient than existing RF technologies.

SUMMARY OF THE INVENTION

The present invention provides supply lines and portable plasma systems that use microwave energy as the heating mechanism. Utilizing microwaves as a heating mechanism may be one solution to the limitations of portable RF systems. Due to the microwave energy's higher energy density, a more efficient portable plasma source can be generated using less energy than RF systems. Also, due to the lower amount of energy required to generate the plasma, the microwave power may be transmitted through a coaxial cable included in the supply lines instead of costly and rigid waveguides. Accordingly, the usage of a coaxial cable to transmit the power can provide flexible operations of plasma discharge unit movements. In addition, the coaxial cable may be combined with one or more gas lines to form a compact supply line that provides gas and microwaves to the plasma discharge unit.

According to one aspect of the present invention, a supply unit comprises a microwave coaxial cable for transmitting microwaves; at least one gas line for transmitting a flow of gas; and an attachment member for positioning the at least one gas line at a predetermined position relative to the microwave coaxial cable.

According to another aspect of the present invention, a supply unit comprises an attachment member having at least one passageway at least partially extending in the attachment member and being configured to transmit a flow of gas therethrough; and a microwave coaxial cable having a portion disposed in the attachment member and being configured to transmit microwaves therethrough.

According to another aspect of the present invention, a supply unit comprises an attachment member; at least one passageway having a portion connected to said attachment member and being configured to transmit a flow of gas therethrough; and a microwave coaxial cable having a portion disposed in said attachment member and being configured to transmit microwaves therethrough.

According to another aspect of the present invention, a supply unit, comprises a positioning jacket; a microwave coaxial cable disposed within said positioning jacket and configured to transmit microwaves therethrough; and at least one gas line interposed between said positioning jacket and said microwave coaxial cable and configured to transmit a flow of gas.

According to yet another aspect of the present invention, a supply line comprises a positioning jacket forming a gas flow channel; a microwave coaxial cable axially disposed within said positioning jacket and configured to transmit microwave; and a plurality of centering disks interposed between said positioning jacket and said microwave coaxial cable, each of said plurality of centering disks having an outer rim for engaging said positioning jacket, an inner rim for holding said microwave coaxial cable and a plurality of spokes interconnecting said inner rim with said outer rim.

According to still another aspect of the present invention, a microwave plasma system includes a supply line comprising: at least one gas line adapted to direct a flow of gas therethrough; and a microwave coaxial cable configured to transmit microwaves. The microwave plasma system also includes a gas flow tube adapted to direct a gas flow therethrough and having an outlet portion and an inlet portion configured to couple to said supply line to receive the gas flow therefrom; and a rod-shaped conductor disposed in said gas flow tube and having an end configured to receive microwaves from said microwave coaxial cable and a tapered tip positioned adjacent said outlet portion and configured to focus microwaves traveling through said rod-shaped conductor.

According to further aspect of the present invention, a microwave plasma system comprises a supply line comprising: at least one gas line adapted to direct a flow of gas therethrough; and a microwave coaxial cable having a core conductor configured to transmit microwaves. The microwave plasma system also includes a gas flow tube adapted to direct a gas flow therethrough and having an outlet portion and an inlet portion; a rod-shaped conductor axially disposed in said gas flow tube, said rod-shaped conductor having an end configured to receive microwaves and a tapered tip positioned adjacent said outlet portion and configured to focus microwaves traveling through said rod-shaped conductor; and an interface portion. The interface portion comprises a gas flow duct having an outlet portion configured to operatively couple to said inlet portion of said gas flow tube and an inlet portion configured to operatively couple to said supply line; and a conductor segment axially disposed within said gas flow duct, said conductor segment being configured to interconnect said end of said rod-shaped conductor with said core conductor.

According to a further aspect of the present invention, a microwave plasma system comprises a microwave source; a waveguide-to-coax adapter having an inlet and a microwave coaxial outlet connector; a waveguide interconnecting said microwave source with said inlet of said waveguide-to-coax adapter; and a supply line. The supply line comprising: at least one gas line adapted to direct a flow of gas therethrough and a microwave coaxial cable having a first end and a second end configured to connect to said microwave coaxial outlet connector. The microwave plasma system includes a gas flow tube adapted to direct a gas flow therethrough and having an outlet portion and an inlet portion configured to couple to said supply line to receive the gas flow therefrom; and a rod-shaped conductor axially disposed in said gas flow tube, said rod-shaped conductor having an end configured to receive microwaves from said first end of said microwave coaxial cable and a tapered tip positioned adjacent said outlet portion of said gas flow tube and configured to focus microwave traveling through said rod-shaped conductor.

According to another further aspect of the present invention, a microwave plasma system comprises a microwave source; a waveguide-to-coax adapter having an inlet and a microwave coaxial outlet connector; a waveguide interconnecting said microwave source with said inlet of said waveguide-to-coax adapter; and a supply line. The supply line comprises at least one gas line adapted to direct a flow of gas therethrough; and a microwave coaxial cable having a core conductor configured to transmit microwave and one end connector configured to connect to said microwave coaxial outlet connector. The microwave plasma system also comprises a gas flow tube adapted to direct a gas flow therethrough and having an outlet portion and an inlet portion; and a rod-shaped conductor axially disposed in said gas flow tube. The rod-shaped conductor has an end configured to receive microwaves from said first end of said microwave coaxial cable and a tapered tip positioned adjacent said outlet portion of said gas flow tube and configured to focus microwave traveling through said rod-shaped conductor. The microwave plasma system also includes an interface portion. The interface portion comprises a gas flow duct having an outlet portion configured to operatively couple to said inlet portion of said gas flow tube and an inlet portion configured to operatively couple to said supply line; and a conductor segment axially disposed within said gas flow duct, said conductor segment being configured to interconnect said end of said rod-shaped conductor with said core conductor.

These and other advantages and features of the invention will become apparent to those persons skilled in the art upon reading the details of the invention as more fully described below.

DETAILED DESCRIPTION OF THE PREFERRED EMBODIMENTS

Unlike existing RF systems, the present invention provides systems that can generate atmospheric plasma using microwave energy. Due to microwave energy's higher energy density, a more efficient portable plasma source can be generated using less energy than the RF systems. Also, due to the lower amount of energy required to generate the plasma, microwave power may be transmitted through a coaxial cable instead of the expensive and rigid waveguides. The usage of the coaxial cable to transmit power can provide flexible operations for the nozzle movements.

Figure 1:
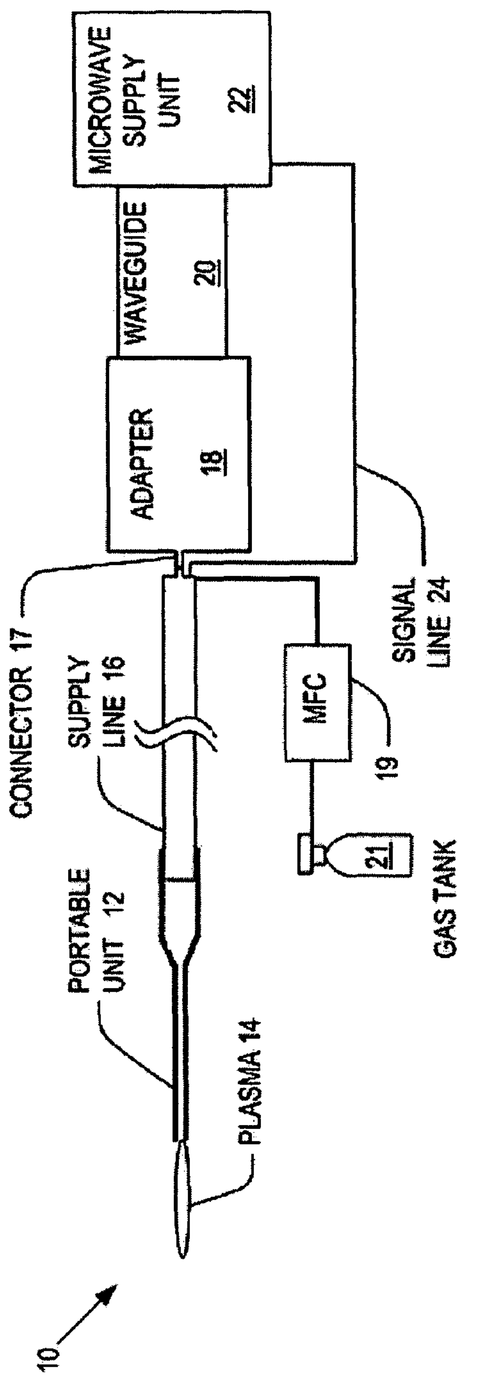
FIG. 1 is a schematic diagram of a system that has a portable microwave plasma discharge unit in accordance with one embodiment of the present invention.

Referring to FIG. 1, FIG. 1 is a schematic diagram of a system 10 that has a portable microwave plasma discharge unit in accordance with one embodiment of the present invention. As illustrated, the system 10 comprises: a microwave supply unit 22 for generating microwaves; a waveguide 20 connected to the microwave supply unit 22; a waveguide-to-coax adapter 18 configured to receive the microwaves within the waveguide 20 and provide the received microwaves through its microwave coaxial connector 17; a portable microwave plasma discharge unit 12 (also called "portable unit") configured to a discharge plasma 14; a supply line 16 for supplying a gas flow and microwaves to the portable microwave plasma discharge unit 12, where the supply line 16 is coupled to a gas tank 21 via a Mass Flow Control (MFC) valve 19 and the waveguide-to-coax adapter 18; and a conductor having at least two conductor signal lines 24 that interconnects an adjustable power control unit 50 (shown in FIG. 3) is mounted on the portable unit 12 (shown in FIG. 3) with a power level control 40 of a power supply 38 (shown in FIG. 2). The waveguide-to-coax adapter 18 is well known in the art and is preferably, but not limited to, WR284 or WR340 which is used in the system 10.

Figure 2:
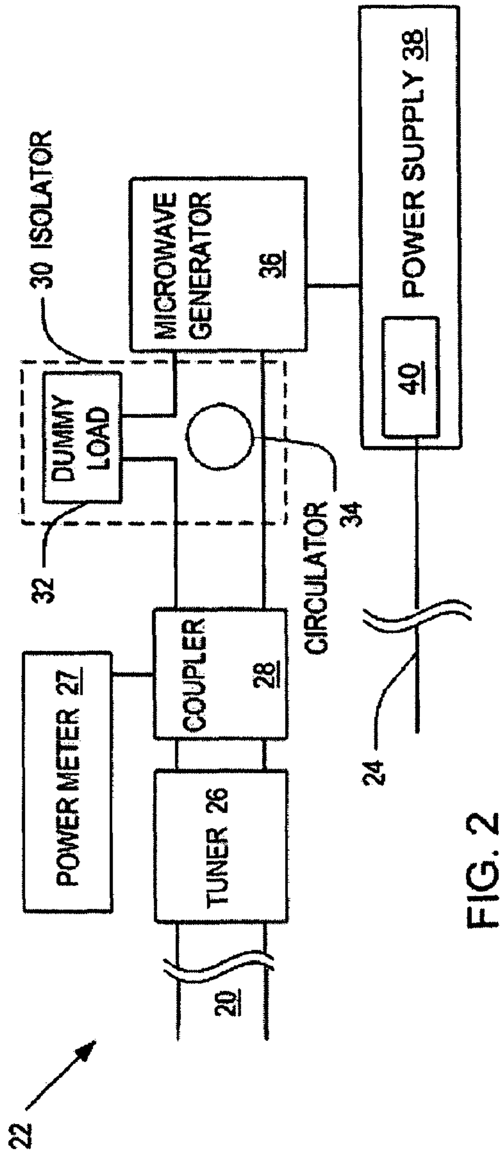
FIG. 2 is a schematic diagram of the microwave supply unit shown in FIG. 1.

FIG. 2 is a schematic diagram of the microwave supply unit 22 shown in FIG. 1. In one embodiment, the microwave supply unit 22 may comprise: a microwave generator 36 connected to the waveguide 20; and the power supply 38 for providing power to the microwave generator 36. The power supply 38 includes the power level control 40 connected to the adjustable power control unit 50 (shown in FIG. 3) via the conductor having at least two signal lines 24.

In another embodiment, the microwave supply unit 22 may comprise: the microwave generator 36 connected to the waveguide 20; the power supply 38 for the microwave generator 36; an isolator 30 comprising a dummy load 32 configured to dissipate retrogressing microwaves that travel toward a microwave generator 36 and a circulator 34 for directing the retrogressing microwaves to the dummy load 32; a coupler 28 for coupling the microwaves and connected to a power meter 27 for measuring the microwave fluxes; and a tuner 26 to reduce the amount of the retrogressing microwaves.

The components of the microwave supply unit 22 shown in FIG. 2 are well known to those skilled in the art and are provided for exemplary purposes only. Thus, it should also be apparent to one skilled in the art that a system with a capability to provide microwaves to the waveguide 20 may replace the microwave supply unit 22 without deviating from the present invention.

Figure 3:
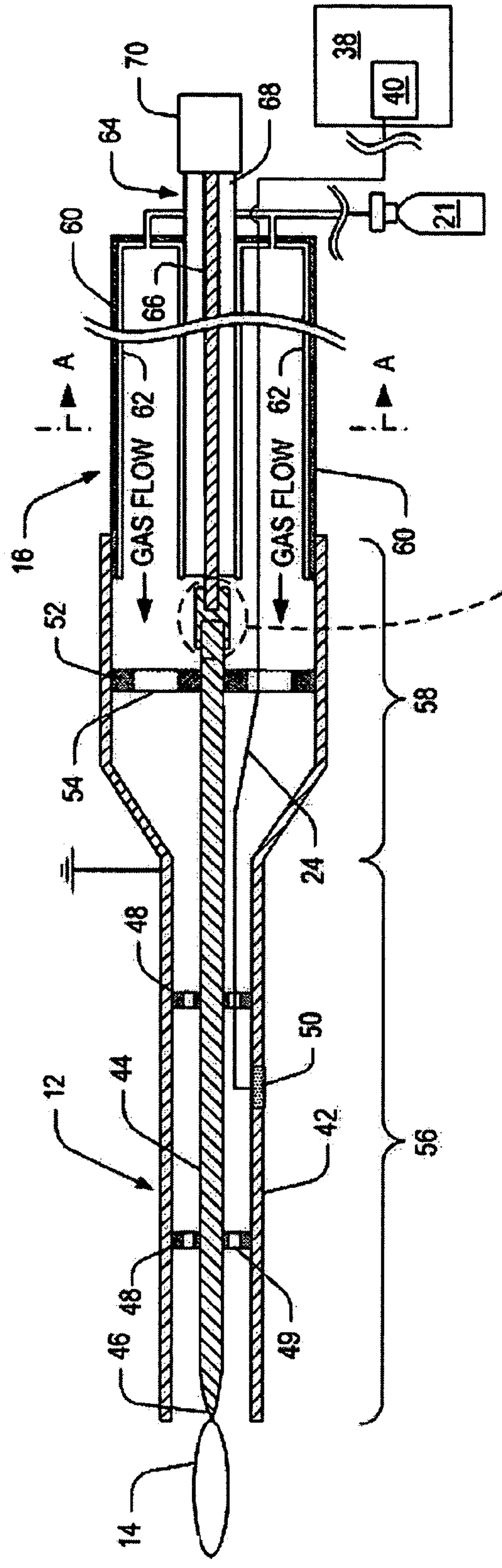
FIG. 3 is a partial cross-sectional view of the portable microwave plasma discharge unit and a supply line shown in FIG. 1.

FIG. 3 is a schematic cross-sectional view of the portable unit 12 and the supply line 16 shown in FIG. 1. The portable unit 12 comprises: a gas flow tube 42 configured to receive a gas flow from at least one gas line 62 of the supply line 16; a rod-shaped conductor 44, axially disposed in the gas flow tube 42, having a tapered tip 46; one or more centering disks 48, each disk having at least one through-pass hole 49; the adjustable power control unit 50 for operating the power level control 40 of the power supply 38; the at least two conductor signal lines 24 interconnecting the adjustable power control unit 50 and the power level control 40; and a holder 52 for securing the rod-shaped conductor 44 to the gas flow tube 42, where the holder 52 has at least one through-pass hole 54. The centering disks 48 may be made of any microwave-transparent dielectric material, such as ceramic or high temperature plastic, and have at least one through-pass hole 49. In one embodiment, the through-pass hole 49 may be configured to generate a helical swirl around the rod-shaped conductor 44 to increase the length and stability of a plasma plume 14. The holder 52 may be made of any microwave-transparent dielectric material, such as ceramic or high temperature plastic, and may have any geometric shape that has at least one through-pass holes for fluid communication between the gas flow tube 42 and the gas lines 62 of the supply line 16.

The gas flow tube 42 provides a mechanical support for the overall portable unit 12 and may be made of any conducting and/or dielectric material. As illustrated in FIG. 3, the gas flow tube 42 may comprise a heating section 56 and an interface section 58. A user of the portable unit 12 may hold the heating section 56 during operation of the system 10 and, for purposes of safety, the gas flow tube 42 may be grounded. In general, a cross-sectional dimension of the heating section 56 taken along a direction normal to the longitudinal axis of the heating section 56 may be different from that of the interface section 58. As will be shown later, the cross-sectional dimension of the interface section 58 may be determined by the dimension of the supply line 16, while the dimension of the heating section 56 may be determined by various operational parameters, such as plasma ignition and stability. As shown in FIG. 3, the gas flow tube 42 is sealed tightly and coupled to the supply line 16. Various coupling mechanisms, such as an o-ring between the inner surface of the gas flow tube 42 and outer surface of the supply line 16, may be used for sealing and providing a secure coupling between the gas flow tube 42 and the supply line 16.

In FIG. 3, the heating section 56 is illustrated as a straight tube. However, one skilled in the art can appreciate that the cross-section of the gas flow tube 42 may change along its longitudinal axis.

Figure 4B:
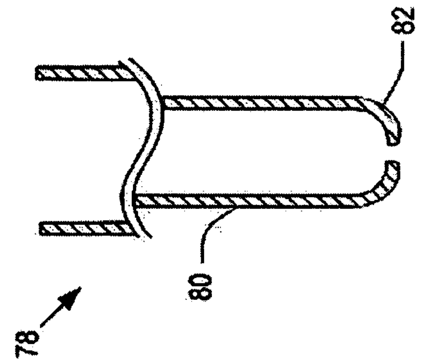
FIGS. 4A-4B are cross-sectional views of alternative embodiments of the gas flow tube shown in FIG. 3.
Figure 4A:
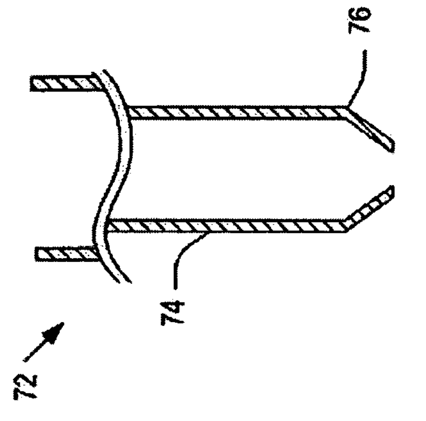

FIG. 4A is a cross-sectional view of an alternative embodiment of a gas flow tube 72 shown in FIG. 3, where a heating section 74 includes a frusto-conical section 76. FIG. 4B is a cross-sectional view of another alternative embodiment of a gas flow tube 78, where a heating section 80 includes a bell-shaped section 82.

Referring back to FIG. 3, the rod-shaped conductor 44 may be made of any conducting material and is configured to receive microwaves from a core conductor 66 of a microwave coaxial cable 64 in the supply line 16. The core conductor 66 may be shielded by an outer layer 68 that may have multiple sublayers. (Detailed description of the outer layer 68 will be given in FIG. 9.) As illustrated in the enlarged schematic diagram 53, a plug-mating connection mechanism may be used to provide a secure connection between the rod-shaped conductor 44 and the core conductor 66. The end portion of the microwave coaxial cable 64 may be stripped to expose the core conductor 66 at suitable length, and connected to a mating conductor 45 that may be also connected to the rod-shaped conductor 44. The mating conductor 45 allows the connection between the rod-shaped conductor 44 and core conductor 66 which may have different outer diameters. It should be apparent to those of ordinary skill in the art that other conventional types of connection mechanisms may be used without deviating from the present invention.

The rod-shaped conductor 44 can be made out of copper, aluminum, platinum, gold, silver and other conducting materials. The term rod-shaped conductor is intended to cover conductors having various cross sections such as a circular, oval, elliptical, or an oblong cross section or combinations thereof. It is preferred that the rod-shaped conductor not have a cross section such that two portions thereof meet to form an angle (or sharp point) as the microwaves will concentrate in this area and decrease the efficiency of the device.

Figure 5A:
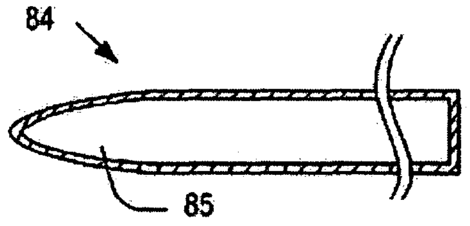
FIGS. 5A-5E are cross-sectional views of alternative embodiments of the rod-shaped conductor shown in FIG. 3.

The rod-shaped conductor 44 includes a tip 46 that focuses the received microwaves to generate the plasma 14 using the gas flowing through the gas flow tube 42. Typically, the microwaves travel along the surface of the rod-shaped conductor 44, where the depth of skin responsible for the microwave migration is a function of a microwave frequency and a conductor material, and this depth can be less than a millimeter. Thus, a hollow rod-shaped conductor 84 of FIG. 5A may be considered as an alternative embodiment for the rod-shaped conductor, wherein the hollow rod-shaped conductor 84 has a cavity 85.

Figure 5B:
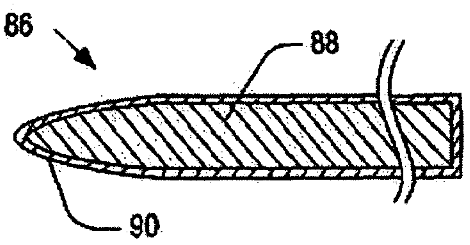

It is well known that some precious metals conduct microwaves better than cheap metals, such as copper. To reduce the unit price of the system without compromising performance of a rod-shaped conductor, the skin layer of the rod-shaped conductor may be made of such precious metals while a cheaper conducting material may be used for the inside core. FIG. 5B is a cross sectional view of another embodiment of a rod-shaped conductor 86, wherein the rod-shaped conductor 86 includes a skin layer 90 made of precious metal(s) and a core layer 88 made of a cheaper conducting material.

Figure 5C:
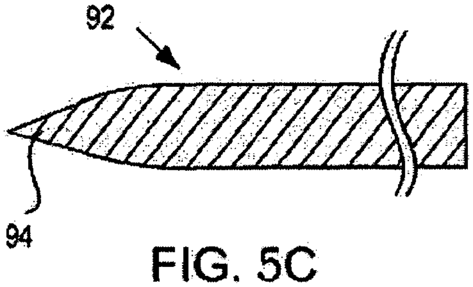

FIG. 5C is a cross-sectional view of yet another embodiment of a rod-shaped conductor 92, wherein the rod-shaped conductor 92 may have a conically-tapered tip 94. Other variations can also be considered. For example, the conically-tapered tip 94 may be eroded faster by plasma than the other portions of the rod-shaped conductor 92, and therefore it may need to be replaced on a regular basis.

Figure 5D:
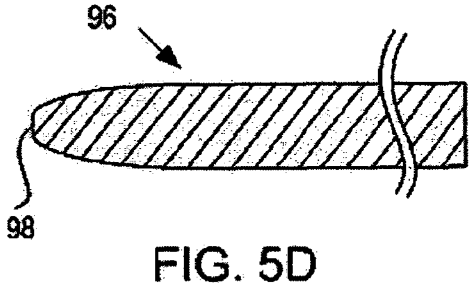

FIG. 5D is a cross sectional view of another embodiment of a rod-shaped conductor 96, wherein a rod-shaped conductor 96 has a blunt-tip 98 instead of a pointed tip to increase the lifetime of the rod-shaped conductor 96.

Figure 5E:
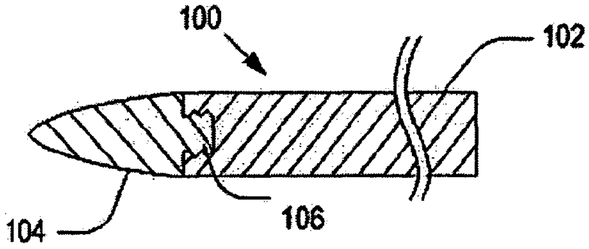

FIG. 5E is a cross sectional view of another embodiment of a rod-shaped conductor 100, wherein the rod-shaped conductor 100 has a tapered section 104 secured to a cylindrical portion 102 by a suitable fastening mechanism 106 (in this case, the tapered section 104 is screwed into the cylindrical portion 102) for easy and quick replacement. Also, it is well known that the microwaves are focused at sharp points or corners. Thus, it is important that the surface of a rod-shaped conductor has various smooth curvatures throughout except in the area of the tapered tip where the microwaves are focused and dissipated.

Now, referring back to FIG. 3, the supply line 16 comprises: an outer jacket 60 coupled and sealed tightly to the interface section 58; one or more gas lines 62, connected to the gas tank 21 via the MFC valve 19 (shown in FIG. 1), for providing the gas flow to the portable unit 12; a microwave coaxial cable 64 that comprises a core conductor 66 and an outer layer 68, where one end of the microwave coaxial cable 64 is coupled to the connector 70. The connector 70 is configured to couple to the counterpart connector 17 of the waveguide-to-coax adapter 18. The connectors 17 and 70 may be, but are not limited to, BNC, SMA, TMC, N, or UHF type connectors.

Figures 6A, 6B, 6C, 7:
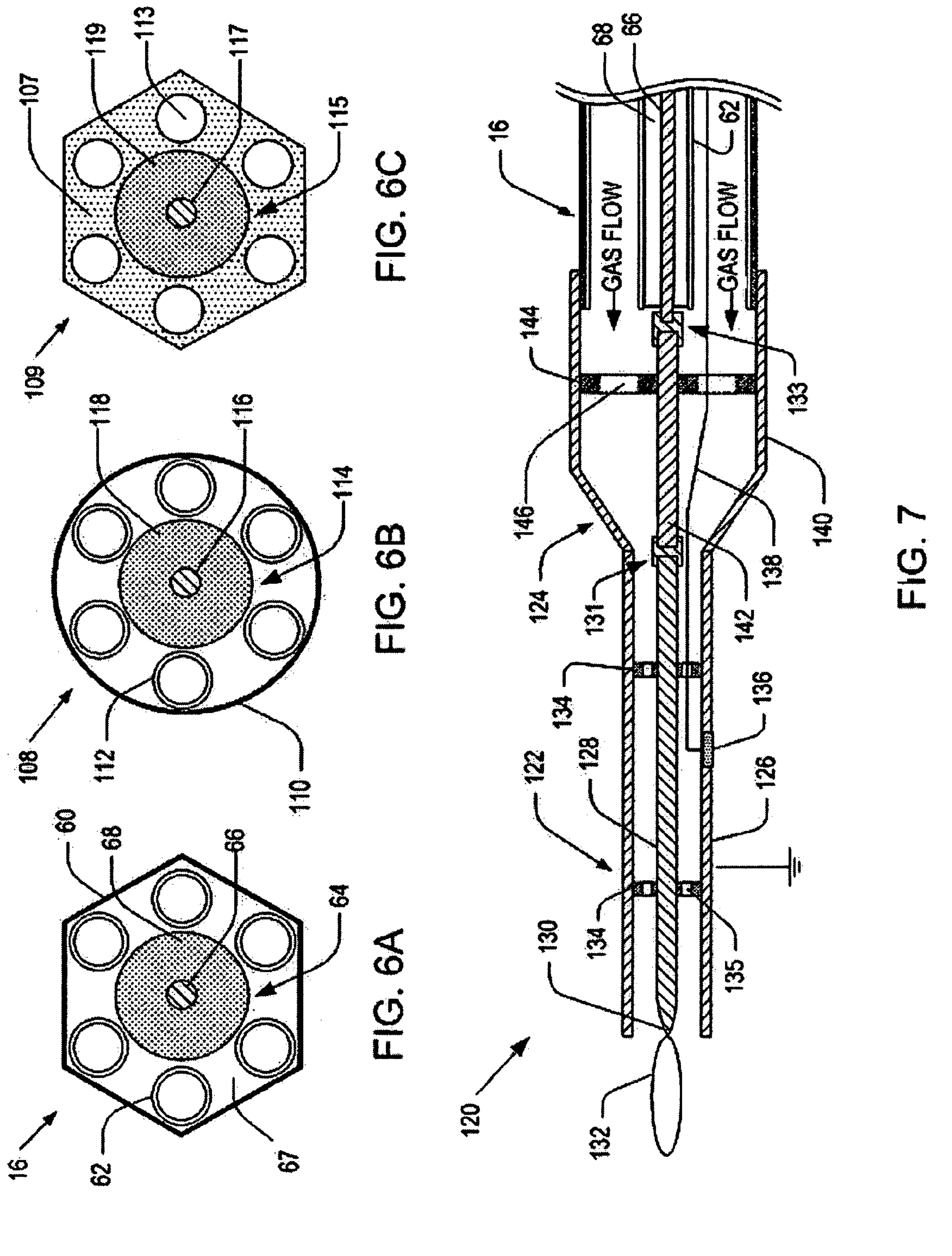
FIGS. 6A-6C are cross-sectional views of the supply line shown in FIG. 3.
FIG. 7 is a cross-sectional view of an alternative embodiment of the portable microwave plasma discharge unit shown in FIG. 3.

FIG. 6A is a schematic cross-sectional view of the supply line 16 taken along the direction A-A in FIG. 3. An outer jacket 60 and the gas lines 62 may be made of any flexible material, where the material is preferably, but not limited to, a conventional dielectric material, such as polyethylene or plastic. Since the outer jacket 60 is coupled to the inner surface of the interface section 58, the interface section 58 may have a similar hexagonal cross-section as the outer jacket 60. In FIG. 6A, each gas line 62 is described as a circular tube. However, it should be apparent those skilled in the art that the number and cross-sectional shape of the gas lines 62 can vary without deviating from the present invention. The at least two conductor signal lines 24 (shown in FIG. 3) may be positioned in a space 67 between the gas lines 62. The detailed description of the microwave coaxial cable 64 will be given below.

FIG. 6B is an alternative embodiment of a supply line 108, having components which are similar to their counterparts in FIG. 6A. This embodiment comprises: an outer jacket 110; one or more gas lines 112; a microwave coaxial cable 114 that includes a core conductor 116 and an outer layer 118. In this embodiment, the interface section 58 may have a circular cross-section to receive a supply line 108.

As illustrated in FIGS. 6A-B, one of the functions of the outer jackets 60 and 110 is positioning the gas lines 62 and 112 with respect to the microwave coaxial cables 64 and 114, respectively, such that the gas lines and the coaxial cable may form a supply line unit. As a variation, the supply line may include a gas line(s), microwave coaxial cable and an attachment member that encloses a portion of the gas line(s) and the microwave coaxial cable. In such a configuration, the attachment member may function as a positioning mechanism that detachably fastens the gas line(s) to the microwave coaxial cable. It is also possible to position the gas line relative to the microwave coaxial cable by a clip or tape or other type of attachment without using a specific outer jacket.

FIG. 6C is another embodiment of a supply line 109. This embodiment comprises: a microwave coaxial cable 115 that includes a core conductor 117 and an outer layer 119; a molding member 107 having at least one gas passage 113 and enclosing the microwave coaxial cable 115. In an alternative embodiment, the supply line 109 may also include an outer jacket.

FIG. 7 is a schematic cross-sectional view of an alternative embodiment of a portable microwave plasma discharge unit 120. In this embodiment, a portable unit 120 includes two portions; a heating portion 122 and an interface portion 124, where the interface portion 124 may accommodate the heating portion 122 having various dimensions. The heating portion 122 comprises: a gas flow tube 126 made of conducting and/or dielectric material; a rod-shaped conductor 128 axially disposed in the gas flow tube 126 and configured to receive microwaves and focus the received microwaves at its tip 130 to generate a plasma 132; a plurality of centering disks 134 having at least one through-pass hole 135; an adjustable power control unit 136; and a conductor having at least two conductor signal lines 138 that interconnect the adjustable power control unit 136 and the power level control 40 (shown in FIG. 3). The interface portion 124 comprises: a gas flow duct 140 made of a conducting and/or dielectric material and is sealingly coupled to the gas flow tube 126; a conductor segment 142 that interconnects the rod-shaped conductor 128 and the core conductor 66 of the supply line 16; and a holder 144 configured to secure the conductor segment 142 to the gas flow duct 140 in a fixed position and having at least one through-pass hole 146 for fluid communication between the gas lines 62 and the gas flow tube 126. A typical plug-mating connection between the rod-shaped conductor 128 and the conductor segment 142 may be used to provide a secure connection. For purposes of operational safety, the gas flow tube 126 and gas flow duct 140 may be grounded.

A plug-mating connection 131 between the rod-shaped conductor 128 and the conductor segment 142 may be used to provide a secure connection. Likewise, a plug-mating connection 133 may be used to provide a secure connection between the conductor segment 142 and the core conductor 66. It should be apparent to those of ordinary skill in the art that other types of connections may be used to connect the conductor segment 142 with the rod-shaped conductor 128 and the core conductor 66 without deviating from the present invention.

It is well known that microwaves travel along the surface of a conductor. The depth of skin responsible for microwave migration is a function of microwave frequency and conductor material, and can be less than a millimeter. Thus, the diameters of the rod-shaped conductor 128 and the conductor segment 142 may vary without deviating from the present invention as long as they are large enough to accommodate the microwave migration.

Figure 8A:
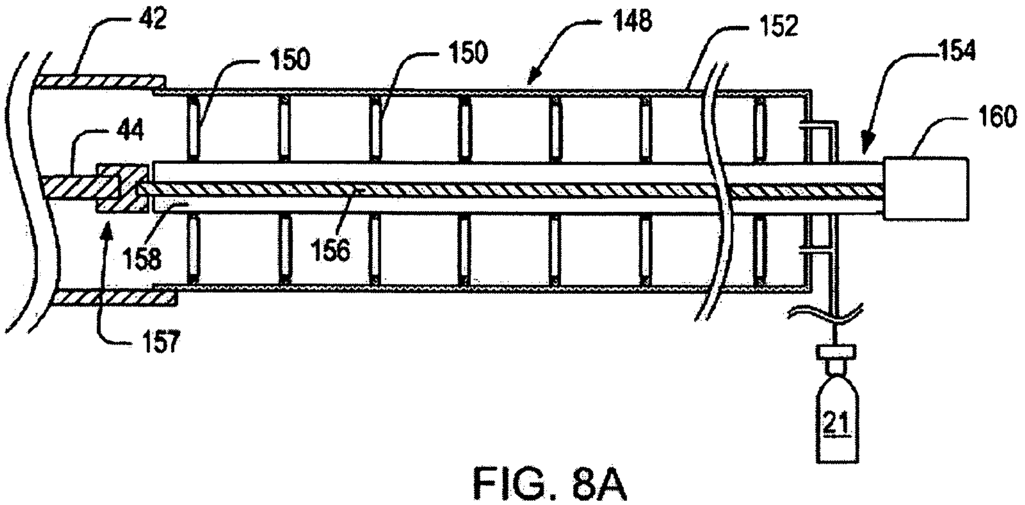
FIG. 8A is a cross-sectional view of an alternative embodiment of the supply line shown in FIG. 3.

FIG. 8A is a schematic cross-sectional view of an alternative embodiment of a supply line 148. As illustrated in FIG. 8A, the supply line 148 comprises: an outer jacket 152 connected to the gas tank 21 via the MFC 19 (shown in FIG. 1); a plurality of centering disks 150; and a microwave coaxial cable 154 that comprises a core conductor 156 and an outer layer 158; where one end of the microwave coaxial cable 154 is coupled to the connector 160. The outer layer 158 may have sublayers that are similar to those of the layer 68. The connector 160 is configured to be coupled to the counterpart connector 17 of the adapter 18. A plug-mating connection 157 between the rod-shaped conductor 44 and the core conductor 156 may be used to provide a secure connection.

Figure 8B:
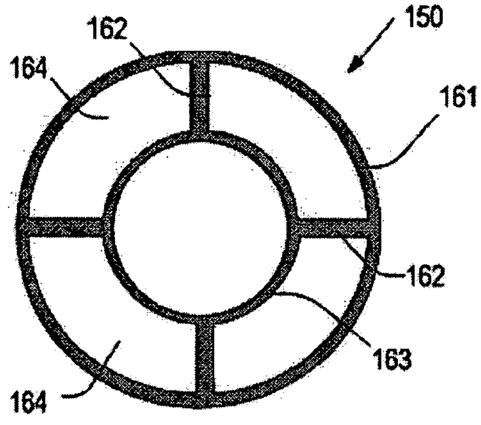
FIG. 8B is a schematic diagram of a centering disk viewed in the longitudinal direction of the supply line shown in FIG. 8A.

FIG. 8B is a schematic diagram of the centering disk 150 viewed in the longitudinal direction of the outer jacket 152. As illustrated in FIG. 8B, the outer rim 161 and the inner rim 163 are connected by four spokes 162 forming spaces 164. The outer jacket 152 and the microwave coaxial cable 154 engage an outer perimeter of the outer rim 161 and an inner perimeter of the inner rim 163, respectively. It should be apparent to those skilled in the art that the number and shape of the spokes 162 can vary without deviating from the present invention.

Figure 9:
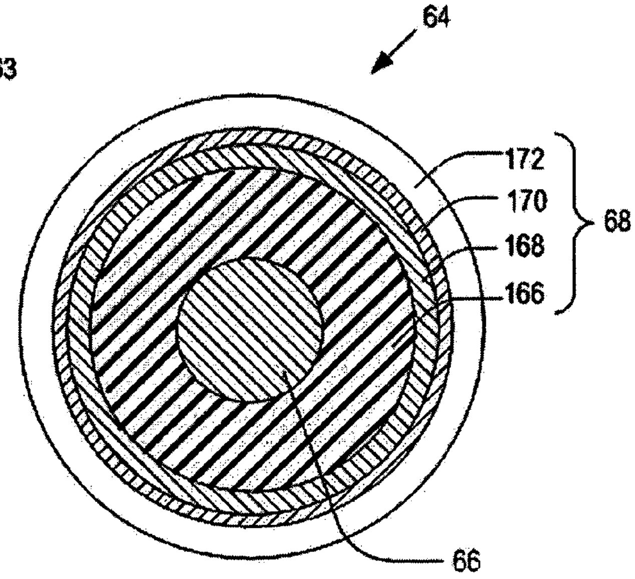
FIG. 9 (PRIOR ART)
FIG. 9 is a cross-sectional view of a typical microwave coaxial cable that may be used in the present invention.

FIG. 9 is a schematic cross-sectional view of the microwave coaxial cable 64, which may be a conventional type known in the art. As illustrated in FIG. 9, the microwave coaxial cable 64 comprises: the core conductor 66 that transmits microwaves and an outer layer 68 that shields the core conductor 66. The outer layer 68 may comprise: a dielectric layer 166; a metal tape layer 168 comprising a conducting material which is configured to shield a dielectric layer 166; a braid layer 170 for providing additional shielding; and an outer jacket layer 172. In one embodiment, the dielectric layer 166 may be comprised of a cellular dielectric material that has a high dielectric constant. The metal tape layer 168 may be made of any metal, and preferably is aluminum or copper, but is not limited thereto.

Figure 10:
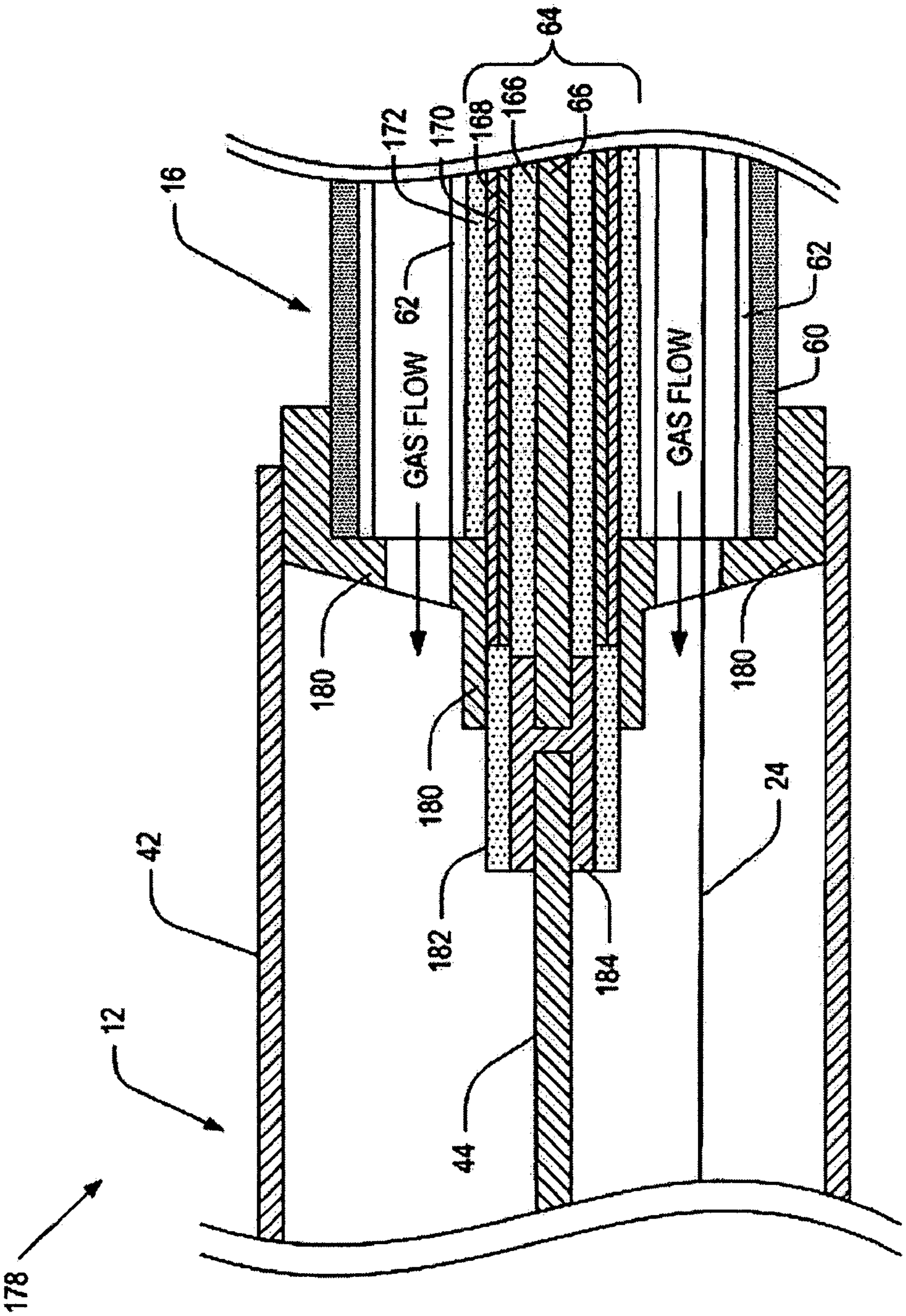
FIG. 10 is a schematic diagram illustrating an interface region where a portable unit is coupled to a supply line in accordance with one embodiment of the present invention.

FIG. 10 is a schematic diagram illustrating an interface region 178 where a portable unit 12 is coupled to a supply line 16 in accordance with one embodiment of the present invention. The supply line 16 may include: a microwave coaxial cable 64 and gas lines 62, where the microwave coaxial cable 64 may include core conductor 66; dielectric layer 166; metal tape layer 168; braid layer 170 and outer jacket layer 172. The rod-shaped conductor 44 may be connected to the core conductor 66 by a mating conductor 184. Grounded cable holder 180 made of a conducting material may connect the gas flow tube 42 with the braid layer 170 so that the gas flow tube 42 is grounded via the braid layer 170. The mating conductor 184 may be insulated from the grounded cable holder 180 by a dielectric layer 182. The dielectric layer 182 may be comprised of a dielectric material, preferably polyethylene.

While the present invention has been described with a reference to the specific embodiments thereof, it should be understood, of course, that the foregoing relates to preferred embodiments of the invention and that modifications may be made without departing from the spirit and the scope of the invention as set forth in the following claims.

What is claimed is:

1. A supply unit for use with a portable unit including:

a gas flow tube made of a conducting material and adapted to direct a gas flow therethrough and having an outlet portion and an inlet portion;

a rod-shaped conductor disposed in said gas flow tube and having a rear end and front end, said front end positioned adjacent said outlet portion, and configured to focus microwaves traveling through said rod-shaped conductor, said rod-shaped conductor extending along an axis of said gas flow tube;

a connector disposed around the rear end of said rod-shaped conductor and connected with said gas flow tube, said connector being made of a conducting material;

said supply unit comprising:

a microwave coaxial cable for transmitting microwaves, said microwave coaxial cable including:

a core conductor and a ground conductor around said core conductor by way of a dielectric layer, a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor;

at least one gas line for transmitting a flow of gas, said gas line being connectable with said gas flow tube; and an attachment member for positioning said at least one gas line at a predetermined position relative to said microwave coaxial cable.

2. A supply unit as defined in claim 1, wherein said at least one gas line is provided as a through passage formed in said attachment member.

3. A supply unit for use with a portable unit including: a gas flow tube made of a conducting material and adapted to direct a gas flow therethrough and having an outlet portion and an inlet portion; a rod-shaped conductor disposed in said gas flow tube and having a rear end and a front end, said front end positioned adjacent said outlet portion, and configured to focus microwaves traveling through said rod-shaped conductor, said rod-shaped conductor extending along an axis of said gas flow tube; a connector disposed around the rear end of said rod-shaped conductor and connected with said gas flow tube, said connector being made of a conducting material; said supply unit comprising:

an attachment member having at least one passageway at least partially extending in said attachment member and being configured to transmit a flow of gas therethrough, said at least one passageway being connectable with said gas flow tube; and a microwave coaxial cable having a portion disposed in said attachment member and being configured to transmit microwaves therethrough, said microwave coaxial cable including a core conductor and a ground conductor around said core conductor by way of a dielectric layer, a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor.

4. A supply unit for use with a portable unit including: a gas flow tube made of a conducting material and adapted to direct a gas flow therethrough and having an outlet portion and an inlet portion; a rodshaped conductor disposed in said gas flow tube and having a rear end and a front end, said front end positioned adjacent said outlet portion, and configured to focus microwaves traveling through said rod-shaped conductor, said rod-shaped conductor extending along an axis of said gas flow tube; a connector disposed around the rear end of said rod-shaped conductor and connected with said gas flow tube, said connector being made of a conducting material; said supply unit comprising:

an attachment member;

at least one passageway having a portion connected to said attachment member and being configured to transmit a flow of gas therethrough, and being connectable with said gas flow tube; and a microwave coaxial cable having a portion disposed in said attachment member and being configured to transmit microwaves therethrough, said microwave coaxial cable including a core conductor and a ground conductor around said core conductor by way of a dielectric layer, a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor.

5. A supply line for use with a portable unit including: a gas flow tube made of a conducting material and adapted to direct a gas flow therethrough and having an outlet portion and an inlet portion; a rod-shaped conductor disposed in said gas flow tube and having a rear end and a front end, said front end positioned adjacent said outlet portion, and configured to focus microwaves traveling through said rod-shaped conductor, said rod-shaped conductor extending along an axis of said gas flow tube; a connector disposed around the rear end of said rod-shaped conductor and connected with said gas flow tube, said connector being made of a conducting material; said supply line comprising:

a positioning jacket;

a microwave coaxial cable disposed within said positioning jacket and configured to transmit microwaves therethrough, said microwave coaxial cable including a core conductor and a ground conductor around said core conductor by way of a dielectric layer, a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor; and at least one gas line interposed between said positioning jacket and said microwave coaxial cable and configured to transmit a flow of gas, and being connectable with said gas flow tube.

6. A supply line as recited in claim 5, wherein said positioning jacket comprises a dielectric material.

7. A supply line as recited in claim 5, wherein said gas line comprises a dielectric material.

8. A supply line for use with a portable unit including: a gas flow tube made of a conducting material and adapted to direct a gas flow therethrough and having an outlet portion and an inlet portion; a rod-shaped conductor disposed in said gas flow tube and having a rear end and a front end, said front end positioned adjacent said outlet portion, and configured to focus microwaves traveling through said rod-shaped conductor, said rod-shaped conductor extending along an axis of said gas flow tube; a connector disposed around the rear end of said rod-shaped conductor and connected with said gas flow tube, said connector being made of a conducting material; said supply line comprising:

a positioning jacket forming a gas flow channel, said gas flow channel being connectable with said gas flow tube;

a microwave coaxial cable axially disposed within said positioning jacket and configured to transmit microwave, said microwave coaxial cable including a core conductor and a ground conductor around said core conductor by way of a dielectric layer, a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor; and a plurality of centering disks interposed between said positioning jacket and said microwave coaxial cable, each of said plurality of centering disks having an outer rim for engaging said positioning jacket, an inner rim for holding said microwave coaxial cable and a plurality of spokes interconnecting said inner rim with said outer rim.

9. A supply line as recited in claim 8, wherein said positioning jacket has a circular cross section.

10. A supply line as recited in claim 8, wherein said positioning jacket comprises a dielectric material.

11. A supply unit for use with a portable unit including:

a gas flow tube made of a conducting material and adapted to direct a gas flow therethrough and having an outlet portion and an inlet portion;

a rod-shaped conductor disposed in said gas flow tube and having a rear end and a front end, said front end positioned adjacent said outlet portion, and configured to focus microwaves traveling through said rod-shaped conductor, said rod-shaped conductor extending along an axis of said gas flow tube;

a connector disposed around the rear end of said rod-shaped conductor and connected with said gas flow tube, said connector being made of a conducting material;

said supply unit comprising:

a microwave coaxial cable including:

a core conductor and a ground conductor around said core conductor by way of a dielectric layer, a leading end of said microwave coaxial cable being engageable with said connector in a state that a leading end of said core conductor is connected with the rear end of said rod-shaped conductor, that is provided in said gas flow tube, in such a manner that said rod-shaped conductor being co-axially provided with said core conductor via a mating connector which concentrically holds said rear end of the rod-shaped conductor and said leading end of said core conductor, and a leading end of said ground conductor is connected with said connector so that said gas flow tube is grounded via the connector to said ground conductor;

at least one gas line for transmitting a flow of gas, said gas line being connectable with said gas flow tube; and an attachment member for positioning said at least one gas line at a predetermined position relative to said microwave coaxial cable.

12. The supply unit according to claim 11, wherein said mating connector has a first end and a second end and said first end is formed with a receptacle indent into which said rear end of the rod-shaped conductor is inserted and said second end is formed with a receptacle indent into which said leading end of said core conductor is inserted.

13. A microwave plasma system, comprising:

a supply line including:

at least one gas line adapted to direct a flow of gas therethrough; and a microwave coaxial cable configured to transmit microwaves, and including a core conductor and a ground conductor around said core conductor by way of a dielectric layer;

a tube unit including:

a gas flow tube made of a conducting material and adapted to direct a gas flow therethrough and having an outlet portion and said gas flow tube being configured to couple to said supply line to receive the gas flow therefrom; and a rod-shaped conductor disposed in said gas flow tube and extending along an axis of said gas flow tube, and having a rear end configured to receive microwaves from said microwave coaxial cable and a front end positioned adjacent said outlet portion and configured to focus microwaves traveling through said rod-shaped conductor; and a connector disposed around the rear end of said rod-shaped conductor and connected with said gas flow tube, said connector being made of a conducting material, said connector allowing said core conductor to connect with the rear end of said rod-shaped conductor in a state of connecting with said ground conductor; and a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor.

14. A microwave plasma system as recited in claim 13, further comprising:

at least one centering, disk located within said gas flow tube for securing said rodshaped conductor to said gas flow tube, said at least one centering disk having at least one through-pass hole; and a holder located within said gas flow tube for positioning said rod-shaped conductor relative to said gas flow tube, said holder having at least one through-pass hole.

15. A microwave plasma system as recited in claim 14, wherein said at least one through-pass hole of said at least one centering disk is configured and disposed for imparting a helical shaped flow direction around said rod-shaped conductor to a gas passing along said at least one through-pass hole.

16. A microwave plasma system as recited in claim 13, wherein said supply line is separable from said tube unit.

17. A microwave plasma system as recited in claim 13, further comprising:

an adjustable power control unit operatively connected to said gas flow tube for controlling transmission of microwaves through said microwave coaxial cable.

18. A microwave plasma system as recited in claim 17, further comprising:

a two or more-conductor signal line interconnecting said adjustable power control unit with a power level control of a microwave supply unit, wherein said microwave supply unit provides the microwaves through said microwave coaxial cable.

19. A microwave plasma system as recited in claim 13, wherein said at least one gas line of said supply line includes a positioning jacket and wherein said microwave coaxial cable is axially disposed in said positioning jacket, said supply line further comprising:

a plurality of centering disks interposed between said positioning jacket and said microwave coaxial cable, each of said centering disks having an outer rim for engaging said positioning jacket, an inner rim for holding said microwave coaxial cable and a plurality of spokes interconnecting said inner rim with said outer rim.

20. A microwave plasma system as recited in claim 13, said supply line further comprising:

a positioning jacket, wherein said microwave coaxial cable is axially disposed within said positioning jacket and said at least one gas line is interposed between said positioning jacket and said microwave coaxial cable along an axial direction of said positioning jacket.

21. A microwave plasma system, comprising:

a supply line including:

at least one gas line adapted to direct a flow of gas therethrough; and a microwave coaxial cable having a core conductor and a ground conductor around said core conductor by way of a dielectric layer, and configured to transmit microwaves;

a tube unit including:

a gas flow tube made of a conducting material and adapted to direct a gas flow therethrough and having an outlet portion and an inlet portion;

a rod-shaped conductor axially disposed in said gas flow tube and extending along an axis of said gas flow tube, said rod-shaped conductor having a rear end configured to receive microwaves and a front end positioned adjacent to said outlet portion and configured to focus microwaves traveling through said rod-shaped conductor; and an interface portion including:

a gas flow duct made of a conducting material and having an outlet portion configured to operatively couple to said gas flow tube and said gas flow duct being operatively coupled to said supply line; and a conductor segment axially disposed within said gas flow duct, said conductor segment being configured to interconnect said rear end of said rod-shaped conductor with said core conductor: and a connector disposed around an end of said conductor segment and connected with said gas flow duct, said connector being made of a conducting material, said connector allowing said core conductor to connect with an end of said conductor segment in a state of connecting with said ground conductor; and a leading end of said microwave coaxial cable being engageable with said connector in a state that a leading end of said core conductor is connected with the rear end of said rod-shaped conductor, that is provided in said gas flow tube, in such a manner that said rod-shaped conductor is coaxially provided with said core conductor, and a leading end of said ground conductor is connected with said connector so that said gas flow tube is grounded via the connector to said ground conductor.

22. A microwave plasma system as recited in claim 21, further comprising:

at least one centering disk located within said gas flow tube for securing said rod-shaped conductor to said gas flow tube, said at least one centering disk having at least one through-pass hole.

23. A microwave plasma system as recited in claim 22, wherein said at least one through-pass hole is configured and disposed for imparting a helical shaped flow direction around said rod-shaped conductor to a gas passing along said at least one through-pass hole.

24. A microwave plasma system as recited in claim 21, further comprising:

a holder located within said gas flow tube for positioning said conductor segment relative to said gas flow duct, said holder having at least one through-pass hole.

25. A microwave plasma system as recited in claim 21, further comprising:

an adjustable power control unit operatively connected to said gas flow tube for controlling transmission of microwaves through said core conductor.

26. A microwave plasma system as recited in claim 25, further comprising:

a two or more-conductor signal line interconnecting said adjustable power control unit with a power level control of a microwave supply unit, wherein said microwave supply unit transmits microwaves through said core conductor.

27. A microwave plasma system as recited in claim 21, wherein said at least one gas line of said supply line includes a positioning jacket and wherein said microwave coaxial cable is axially disposed in said positioning jacket, said supply line further comprising:

a plurality of centering disks interposed between said positioning jacket and said microwave coaxial cable, each of said centering disks having an outer rim for engaging said positioning jacket, an inner rim for holding said microwave coaxial cable and a plurality of spokes interconnecting said inner rim with said outer rim.

28. A microwave plasma system as recited in claim 21, said supply line further comprising:

a positioning jacket, wherein said microwave coaxial cable is axially disposed within said positioning jacket and said at least one gas line is interposed between said positioning jacket and said microwave coaxial cable along an axial direction of said positioning jacket.

29. A microwave plasma system, comprising:

a microwave source;

a waveguide-to-coax adapter having an inlet and a microwave coaxial outlet connector;

a waveguide interconnecting said microwave source with said inlet of said waveguide-to-coax adapter;

a supply line including:

at least one gas line adapted to direct a flow of gas therethrough; and a microwave coaxial cable having a first end and a second end configured to connect to said microwave coaxial outlet connector, said microwave coaxial cable having a core conductor and a ground conductor around said core conductor by way of a dielectric layer;

a gas flow tube made of a conducting material and adapted to direct a gas flow therethrough and having an outlet portion and said gas flow tube being configured to couple to said supply line to receive the gas flow therefrom; and a rod-shaped conductor axially disposed in said gas flow tube and extending along an axis of said gas flow tube, said rod-shaped conductor having a rear end configured to receive microwaves from said first end of said microwave coaxial cable and a front end positioned adjacent said outlet portion of said gas flow tube and configured to focus microwave traveling through said rod-shaped conductor; and a connector disposed around the rear end of said rod-shaped conductor and connected with said gas flow tube, said connector being made of a conducting material, said connector allowing said core conductor to connect with the rear end of said rod-shaped conductor in a state of connecting with said ground conductor; and a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor.

30. A microwave plasma system as recited in claim 29, wherein said microwave source comprises a microwave generator and a power supply for providing power thereto, said power supply having a power level control.

31. A microwave plasma system as recited in claim 30, further comprising:

an adjustable power control unit operatively connected to said gas flow tube for controlling transmission of microwaves through said microwave coaxial cable.

32. A microwave plasma system as recited in claim 31, further comprising:

a two or more-conductor signal line interconnecting said adjustable power control unit with said power level control.

33. A microwave plasma system as recited in claim 29, further comprising:

an isolator coupled to said waveguide and configured to dissipate retrogressing microwaves that travel toward said microwave source, said isolator including:

a dummy load for dissipating the retrogressing microwaves, and a circulator for diverting the retrogressing microwaves to said dummy load.

34. A microwave plasma system as recited in claim 29, further comprising:

a coupler coupled to said waveguide and connected to a power meter for measuring microwave fluxes.

35. A microwave plasma system as recited in claim 29, further comprising:

at least one centering disk located within said gas flow tube for securing said rodshaped conductor to said gas flow tube, said at least one centering disk having at least one through-pass hole.

36. A microwave plasma system as recited in claim 35, wherein said at least one through-pass hole is configured and disposed for imparting a helical shaped flow direction around said rod-shaped conductor to a gas passing along said at least one through-pass hole.

37. A microwave plasma system as recited in claim 29, wherein said at least one gas line of said supply line includes a positioning jacket and wherein said microwave coaxial cable is axially disposed in said positioning jacket, said supply line further comprising:

a plurality of centering disks interposed between said positioning jacket and said microwave coaxial cable, each of said centering disks having an outer rim for engaging said positioning jacket, an inner rim for holding said microwave coaxial cable and a plurality of spokes interconnecting said inner rim with said outer rim.

38. A microwave plasma system as recited in claim 29, said supply line further comprising:

a positioning jacket, wherein said microwave coaxial cable is axially disposed within said positioning jacket and said at least one gas line is interposed between said positioning jacket and said microwave coaxial cable along an axial direction of said positioning jacket.

39. A microwave plasma system, comprising:

a microwave source;

a waveguide-to-coax adapter having an inlet and a microwave coaxial outlet connector;

a waveguide interconnecting said microwave source with said inlet of said waveguide-to-coax adapter;

a supply line including:

at least one gas line adapted to direct a flow of gas therethrough; and a microwave coaxial cable having a core conductor configured to transmit microwave and a ground conductor around said core conductor by way of a dielectric layer, and having one end connector configured to connect to said microwave coaxial outlet connector;

a gas flow tube made of a conducting material and adapted to direct a gas flow therethrough and having an outlet portion and an inlet portion;

a rod-shaped conductor axially disposed in said gas flow tube and extending along an axis of said gas flow tube, said rod-shaped conductor having a rear end configured to receive microwaves from the other end of said microwave coaxial cable and a front end positioned adjacent said outlet portion of said gas flow tube and configured to focus microwave traveling through said rod-shaped conductor; and an interface portion including:

a gas flow duct made of a conducting material and having an outlet portion configured to operatively couple to said gas flow tube and said gas flow duct being operatively coupled to said supply line; and a conductor segment axially disposed within said gas flow duct, said conductor segment being configured to interconnect said rear end of said rod-shaped conductor with said core conductor: and a connector disposed around an end of said conductor segment and connected with said gas flow duct, said connector being made of a conducting material, said connector allowing said core conductor to connect with an end of said conductor segment in a state of connecting with said ground conductor; and a leading end of said microwave coaxial cable being engageable with said connector in a state that a leading end of said core conductor is connected with the rear end of said rod-shaped conductor, that is provided in said gas flow tube, in such a manner that said rod-shaped conductor is co-axially provided with said core conductor, and a leading end of said ground conductor is connected with said connector so that said gas flow tube is grounded via the connector to said ground conductor.

40. A microwave plasma system as recited in claim 39, wherein said microwave source comprises a microwave generator and a power supply for providing power thereto, said power supply having a power level control.

41. A microwave plasma system as recited in claim 39, further comprising:

an adjustable power control unit operatively connected to said gas flow tube for controlling transmission of microwaves through said microwave coaxial cable.

42. A microwave plasma system as recited in claim 39, further comprising:

a two or more-conductor signal line interconnecting said adjustable power control unit with said power level control.

43. A microwave plasma system as recited in claim 39, further comprising:

an isolator coupled to said waveguide and configured to dissipate retrogressing microwaves that travel toward said microwave source, said isolator including:

a dummy load for dissipating the retrogressing microwaves, and a circulator for diverting the retrogressing microwaves to said dummy load.

44. A microwave plasma system as recited in claim 39, further comprising:

a coupler coupled to said waveguide and connected to a power meter for measuring microwave fluxes.

45. A microwave plasma system as recited in claim 39, further comprising:

at least one centering disk located within said gas flow tube for securing said rod-shaped conductor to said gas flow tube, said at least one centering disk having at least one through-pass hole.

46. A microwave plasma system as recited in claim 45, wherein said at least one through-pass hole is configured and disposed for imparting a helical shaped flow direction around said rod-shaped conductor to a gas passing along said at least one through-pass hole.

47. A microwave plasma system as recited in claim 39, further comprising:

a holder located within said gas flow tube for positioning said conductor segment relative to said gas flow duct, said holder having at least one through-pass hole.

48. A microwave plasma system as recited in claim 39, wherein said at least one gas line of said supply line includes a positioning jacket and wherein said microwave coaxial cable is axially disposed in said positioning jacket, said supply line further comprising:

a plurality of centering disks interposed between said positioning jacket and said microwave coaxial cable, each of said centering disks having an outer rim for engaging said positioning jacket, an inner rim for holding said microwave coaxial cable and a plurality of spokes interconnecting said inner rim with said outer rim.

49. A microwave plasma system as recited in claim 39, said supply line further comprising:

a positioning jacket, wherein said microwave coaxial cable is axially disposed within said positioning jacket and said at least one gas line is interposed between said positioning jacket and said microwave coaxial cable along an axial direction of said positioning jacket.

* * * * *